United States Patent (10) Patent No.: US 11,920,771 B2
Karp et al. (45) Date of Patent: Mar. 5, 2024

(54) MULTI-COLORED NIGHT LIGHT WITH SOUND OUTPUT IMITATING BREATHING PATTERN CADENCE

(71) Applicant: HB Innovations, Inc., Los Angeles, CA (US)

(72) Inventors: Harvey Neil Karp, Los Angeles, CA (US); Peter Fornell, Los Angeles, CA (US)

(73) Assignee: HB Innovations, Inc., Los Angeles, CA (US)

( * ) Notice: Subject to any disclaimer, the term of this patent is extended or adjusted under 35 U.S.C. 154(b) by 0 days.

(21) Appl. No.: 17/519,644

(22) Filed: Nov. 5, 2021

(65) Prior Publication Data

US 2023/0144816 A1 May 11, 2023

(51) Int. Cl.
*F21V 33/00* (2006.01)
*F21S 9/02* (2006.01)
*F21V 23/00* (2015.01)
*F21V 23/04* (2006.01)
*F21V 23/06* (2006.01)
(Continued)

(52) U.S. Cl.
CPC .............. *F21V 23/003* (2013.01); *F21S 9/02* (2013.01); *F21V 23/04* (2013.01); *F21V 23/06* (2013.01); *G06F 3/041* (2013.01); *G06F 3/165* (2013.01); *H04R 1/028* (2013.01); *H04R 3/00* (2013.01); *F21W 2131/30* (2013.01); *F21Y 2113/10* (2016.08); *H04R 2430/01* (2013.01)

(58) Field of Classification Search
CPC .... F21V 23/003; F21V 33/0056; F21L 4/027; F21L 4/08; H05B 45/10; H05B 45/20; H05B 45/305; H05B 47/165
See application file for complete search history.

(56) References Cited

U.S. PATENT DOCUMENTS 3,604,129 A * 9/1971 Eisenberg ................ G06G 7/26
434/266
4,029,954 A 6/1977 Moyer
(Continued)

FOREIGN PATENT DOCUMENTS

AU 2012100114 A4 6/2012
CN 110107842 A 8/2019
(Continued)

OTHER PUBLICATIONS

International Search Report and Written Opinion, PCT/US2022/049007, dated Feb. 16, 2023.

*Primary Examiner* — Ismael Negron
(74) *Attorney, Agent, or Firm* — Akerman LLP (57) ABSTRACT

A device for providing light and sound to a surrounding area configured to output sound and light in combination of a breathing cadence to calm a subject. The device includes a light configured to emit light at varying colors and levels of intensity synchronized with varying volumes of the sound output. The intensity of light output may increase during an inhalation period of the cadence and decrease during an exhalation period of the cadence. The cadence may be adjusted, manually or automatically, or matched to a user's breathing pattern, to provide desired light and sound combination to provide a calming effect. The sound output may be white noise, pink noise, or Brown noise, or a recording of other sounds.

22 Claims, 7 Drawing Sheets

(51) Int. Cl.
*G06F 3/041* (2006.01)
*G06F 3/16* (2006.01)
*H04R 1/02* (2006.01)
*H04R 3/00* (2006.01)
*F21W 131/30* (2006.01)
*F21Y 113/10* (2016.01)

(56) References Cited

U.S. PATENT DOCUMENTS

| | | | |
|---|---|---|---|
| 4,214,185 A | 7/1980 | Breeze | |
| 4,606,328 A | 8/1986 | Thoman | |
| 4,812,827 A | 3/1989 | Scripps | |
| 4,819,616 A | 4/1989 | Samson | |
| 5,174,645 A | 12/1992 | Chung | |
| 5,601,360 A | 2/1997 | Paquette | |
| 6,040,680 A | 3/2000 | Toya | |
| 6,074,199 A | 6/2000 | Song | |
| 6,918,770 B2 | 7/2005 | Odiwo | |
| 7,475,441 B1 | 1/2009 | Soberal | |
| 7,604,378 B2* | 10/2009 | Wolf | H05B 45/325 362/85 |
| 9,103,546 B2* | 8/2015 | Almalki | F21V 14/025 |
| 9,363,592 B2* | 6/2016 | Wen | F21V 33/0056 |
| 9,398,670 B2* | 7/2016 | Kidakarn | H05B 47/155 |
| 9,415,184 B2 | 8/2016 | Julkowski et al. | |
| 9,769,908 B2* | 9/2017 | Saijo | H04R 1/028 |
| 9,784,417 B1* | 10/2017 | Springer | F21V 23/006 |
| 9,854,641 B2* | 12/2017 | Chen | G08B 7/06 |
| 10,201,236 B1 | 2/2019 | Cloud | |
| 10,258,761 B2 | 4/2019 | Smudde | |
| 10,433,041 B2* | 10/2019 | Garrett | H04R 1/025 |
| 10,437,200 B1 | 10/2019 | Ostler | |
| 10,728,640 B2* | 7/2020 | Lee | G10L 17/00 |
| 11,306,910 B1 | 4/2022 | Guedez | |
| 11,353,185 B2 | 6/2022 | Ocegueda | |
| 11,529,493 B2 | 12/2022 | Weiss | |
| 2002/0068501 A1 | 6/2002 | Grinnell et al. | |
| 2004/0130449 A1* | 7/2004 | Hung | G08B 21/0208 340/539.15 |
| 2007/0179334 A1 | 8/2007 | Groves et al. | |
| 2007/0223217 A1 | 9/2007 | Hsu | |
| 2007/0291488 A1 | 12/2007 | Heathcock | |
| 2010/0156326 A1* | 6/2010 | Chen | F21V 33/0056 362/157 |
| 2010/0219697 A1 | 9/2010 | Azancot et al. | |
| 2013/0072764 A1 | 3/2013 | Shtairyd | |
| 2014/0082839 A1 | 3/2014 | Piombino | |
| 2017/0258398 A1 | 9/2017 | Jackson | |
| 2018/0106897 A1 | 4/2018 | Shouldice et al. | |
| 2018/0352633 A1 | 12/2018 | Van De Sluis et al. | |
| 2019/0224444 A1 | 7/2019 | Kalensky | |
| 2020/0069076 A1 | 3/2020 | Lee | |
| 2020/0125036 A1* | 4/2020 | Weiss | H05B 47/19 |
| 2020/0222867 A1 | 7/2020 | Cetinkaya | |
| 2021/0046392 A1 | 2/2021 | Ray et al. | |

FOREIGN PATENT DOCUMENTS

| | | |
|---|---|---|
| CN | 212361871 U | 1/2021 |
| GB | 2475053 A | 5/2011 |
| WO | 2004036774 | 4/2004 |
| WO | 2004069319 | 8/2004 |
| WO | 2009031062 | 3/2009 |
| WO | 2016205373 | 12/2016 |

* cited by examiner

MULTI-COLORED NIGHT LIGHT WITH
SOUND OUTPUT IMITATING BREATHING
PATTERN CADENCE

TECHNOLOGY FIELD

This disclosure generally relates to illumination devices and more particularly to night lights capable of emitting sound.

BACKGROUND

Night lights are common devices used in various rooms in a home to provide a relatively small amount of light to such a room. The lights are often used in a child's room to allow the child a small amount of light when other light sources are turned off, while being dim enough to not interfere with sleeping.

SUMMARY

In one aspect, an illumination device comprises a light source and a speaker combined in a common housing. The light source may be capable of emitting various color of light to the area surrounding the illumination device. The speaker may be capable of producing a variety of sounds to the area surrounding the illumination device. In one embodiment, the speaker emits sound in a cadence representative of a breathing pattern. Such pattern will help calm and relax a child to assist in shortening the time required to reach sleep. By synchronizing the audio pattern with a light pattern, it further enforces the natural response of the child to follow the pattern of the device. A single cycle of the cadence includes a inhalation period and an exhalation period. The volume of the sound output by the speaker may be increased during the inhalation period and decreased during the exhalation period. The luminosity emitted by the light source may also be increased and decreased in synchronization with the increase and decrease of the volume of the sound output by the speaker.

In one embodiment, the sound output by the speaker is white noise, wherein sound at all audible frequencies are produced in equal intensity. In another embodiment, the sound output by the speaker may be selected from the group of white noise, pink noise, and Brown noise, wherein pink noise produces sound at lower intensities in higher frequency ranges and Brown noise produces sounds at even lower intensities than pink noise in the higher frequency ranges. In another embodiment, the sound output by the speaker may be selected from realistic sounds or actual recordings of sounds considered to have a calming effect, including breathing sounds. The housing may further comprise a knob adapted to alter the intensity of sound at the higher frequency ranges, allowing for the selection of desired noise between white noise, pink noise, and Brown noise. In yet another embodiment, the volume of the sound output by the speaker remains constant, while the intensities of sound in the higher frequency ranges changes during the cadence. Thus, the sound output by the speaker may transition from Brown noise to pink noise to white noise during the inhalation period and then transition back from white noise to pink noise to Brown noise during the exhalation period.

In one embodiment, a length of the single cycle of the cadence may be selected between 3 seconds and 7 seconds. The inhalation period may comprise anywhere from 30% to 50% of the single cycle, while the exhalation period may comprise anywhere from 70% to 50% in the single cycle, but such numbers may vary and be tailored to the individual's needs. The length of the cadence and the ratio between inhalation and exhalation may also vary to help bring rapid breathing down (calming effect). In one embodiment, the illumination device comprises buttons or switches, or via an app, allowing for the adjustment of the length of the cadence and a change of a ratio between the length of the inhalation period and the length of the exhalation period. In another embodiment, the illumination device detects and measures the user's breath cadence to provide a sound, light and cadence that provides an optimal calming effect for that user.

The light source may emit light at a maximum intensity at the end of the inhalation period and decrease the intensity of the light to between 30% and 60% of the maximum intensity during the exhale period. In one embodiment, the intensity of the light may decrease during the exhalation period to a point where no light is emitted from the light source. The illumination device may include adjustable settings for controlling lamination and sound output patterns. In one embodiment, the illumination device may allow for the adjustment of the maximum intensity of the light source, by use of buttons, a knob, a slider, an application or through other methods known in the art. In yet another embodiment, the illumination device may comprise an ambient light sensor capable of sensing the presence and level of ambient light surrounding the illumination device. When a low presence of ambient light is detected, the ambient light sensor may instruct the light source to lower the maximum intensity of the light emitted from the light source. When a high presence of ambient light is detected, the ambient light sensor may instruct the light source to increase the maximum intensity of the light emitted from the light source.

The illumination device may further comprise the capability to change a color of the light emitted by the light source. The light source may comprise multiple light emitting diodes (LEDs) of differing colors. The illumination device may comprise a slider, a knob, a button, or an application that allow the light source to cycle through the activation of the different colored LEDs, or combinations thereof, that would allow the light emitted by the light source to produce different colors.

In one embodiment, the housing further comprises a light diffuser surrounding or proximate to the light source. The light diffuser is adapted to soften and evenly scatter the light emitted by the light source, lessening the harshness of the light and creating a more aesthetic and pleasant appearance. The light diffuser may further comprise touch-sensitive capabilities, wherein the light source and/or speaker may be turned on and off through a predetermined pattern of touch. Additionally, the touch-sensitive capabilities of the light diffuser may allow for the change of the maximum luminosity of the light source.

In one embodiment, the illumination device further comprises a communication port configured for wired and/or wireless communication with a remote device. The remote device may be configured with an application, such as a mobile application, configured to interface users operations and/or settings for such operations with respect to the illumination device via the remote device. The communication port may be configured for wireless communication with the remote device to interface operations via suitable wireless communication protocols such as Bluetooth, WiFi or Near-Field Communication (NFC). In a further or another embodiment, the communication port may be configured for wired communication. For example, the remote device may wire directly to the communication port along the housing, such as through the use of a universal serial bus (USB). The application may provide a user interface, which may allow the change of various outputs of the illumination devices, such as altering the volume, increasing or decreasing the maximum intensity of the light, changing the color of the light, setting a schedule for altering the sound or light at specific times or days, or altering the sound output by the speaker. In one embodiment, the application may be used to upload user-selected sounds to the speaker, including pre-recorded music, audiobooks, or soothing sounds such as rainfall. As introduced above, in one embodiment, the communication port may be configured for wireless communication with a remote device via Near-Field Communication (NFC). As the illumination device may be used in close proximity to a child, use of NFC may be used to avoid radiation concerns. Thus, in such an example, a remote device operating an application may interface a user with the operations of the illumination device via NFC.

In one embodiment, the illumination device includes a battery to provide power for the operations of the illumination device while disconnected from a residential power outlet. In one embodiment, the illumination device is configured with a charger to charge the battery. The illumination device may include a charging port to receive a charging plug of a cable or platform. In one example, the charging port comprises electrical contacts for contacting electrical contacts of a charger. In one embodiment, the illumination device comprises or is otherwise configured to receive power from a stand upon which the body or housing of the illumination device may be supported while being powered and/or charged. In one configuration, the stand includes a switch to disable power when the body or housing of the illumination device is not positioned on the stand to receive power. Such a switch may be used to alleviate electrical safety concerns. In one example, the switch comprises a magnetic switch including a small magnet that activates the switch to allow the stand to activate power. Similar functionality could be accomplished with light, presence and or through other methods known in the art.

These and other aspects and advantages of the present disclosure will become better understood with regard to the following description, appended claims, and accompanying drawings.

DETAILED DESCRIPTION

The present disclosure describes an illumination device configured to output light and sound. In one example, the sound is output at a cadence representative of a breathing pattern. In various embodiments, the device may be further configured to synchronize an intensity of the output light with the cadence. For example, the light may increase and decrease in intensity and/or change color during inhale and exhale breathing phases. The device may find particular use with respect to children as a light companion to provide light and soothing sounds to aid in falling asleep or as otherwise required. The device may find use with other subjects such as children, adolescents, adults, or elderly. While various embodiments may be described herein with respect to children, it is to be understood that such descriptions may be equally applicable to other subjects as the present disclosure is not limited to children.

Figure 7:
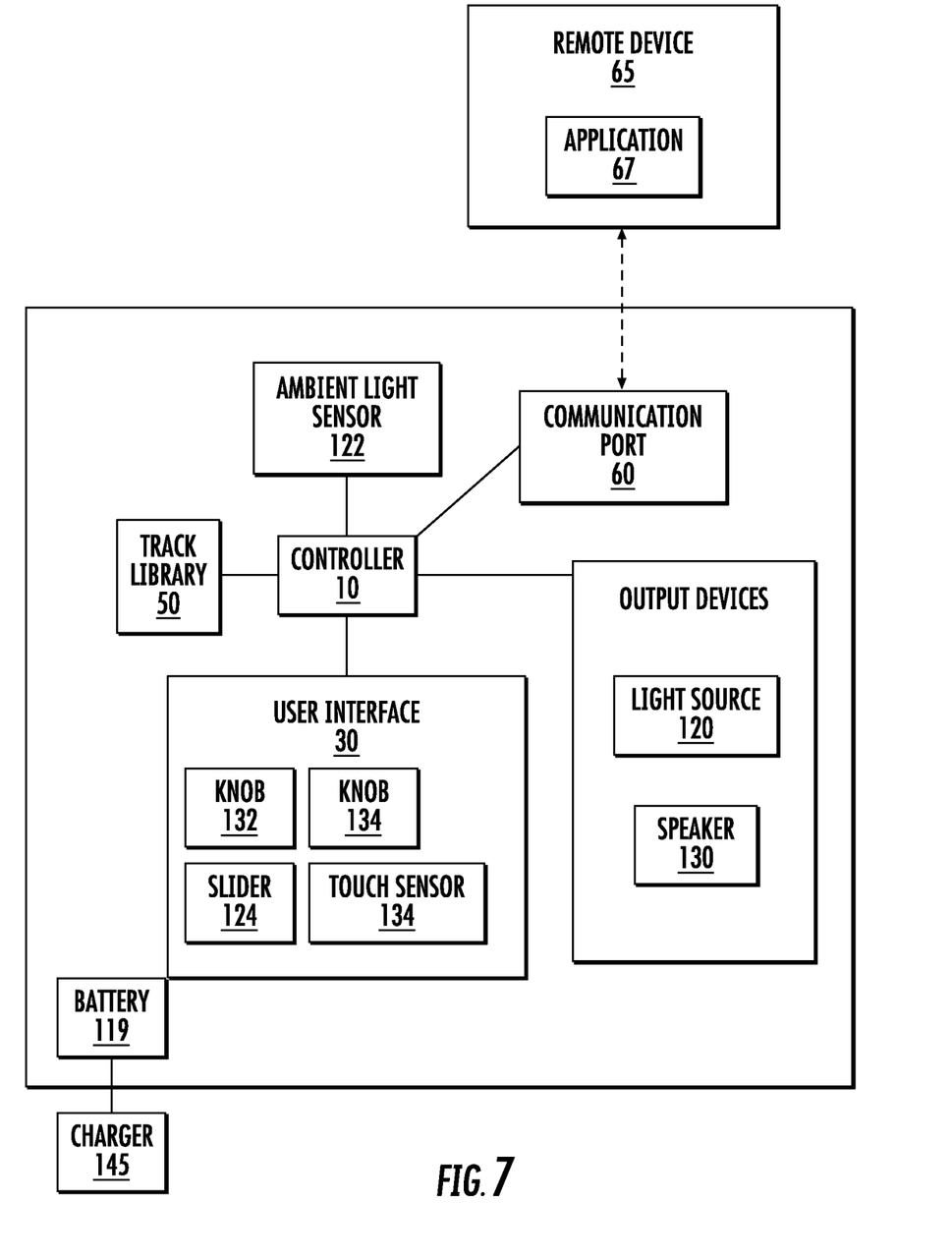
FIG. 7 is a schematic of an embodiment of the illumination device according to various embodiments described herein.

With particular reference to FIG. 7, showing a schematic of an illumination device 100 including various features described herein, the illumination device 100 may include a light source 120 configured to output light and a speaker 130 configured to output sound. The light source 120 may include one or more light sources such incandescent lights, florescent lights, halogen lights, light emitting diodes ("LEDs"), another light source known in the art, or a combination thereof. The light source 120 may be configured to emit light a different frequencies, thereby allowing for the output of different colors of light. In a further or another embodiment, the light source 120 may be configured to display text. In a further or another embodiment, the luminosity/intensity of the light output by the light source 120 may be increased or decreased, e.g., in response to a control signal from a controller 10. Additionally or alternatively, the light source 120 may be configured to emit light at different intensities or intensity patterns and colors or color patterns in response to a control system signal from the controller 10, which may be via user interaction at a user interface 30. The speaker 130 may be capable of producing intelligible speech, music, or noise.

The illumination device 100 may include a track library 50 including one or more tracks for output at speakers 130 and/or lights. The tracks may comprise sound and/or light programs wherein the speakers 130 and/or light source 120, as the case may be, output predefined sound and/or light patterns according to the track. As described in more detail below, sound and light patterns may be synchronized to provide a light pattern corresponding to the sound pattern. For example, initiation of a track may cause the speaker 130 and light source 120 to output synchronized patterns of sound and light according to the track. In some examples, the track causes the speaker 130 or light source 120 to output a predefined sound or light track and the speaker 130 or light source 120 is configured to modulate its output based on the output of the track to provide a corresponding output pattern, e.g., via analog or digital processing of the control signal of the track or the output of the track, thereby synchronizing output.

The illumination device 100 may include a controller 10 configured to control the operations of the illumination device 100 automatically, e.g., according to a programed operation, and/or according to input by a user via the user interface. In one embodiment, the controller 10 includes a clock from which to keep track of time with respect to a schedule, as described in more detail below. In some embodiments, the controller 10 may also keep track of dates with respect to the schedule.

The illumination device 100 may include a user interface 30 configured to interface a user with operations of the illumination device 100 via the controller 10, such as control of lighting output by the light source 120 (e.g., power on/off, color, color pattern, intensity, intensity pattern), sound output by the speaker 130 (e.g., power on/off, sound track, sound type, sound pattern, volume). The user interface 30 may include knobs, buttons, switches, touchscreens, touch sensors, or other suitable structures for interfacing a user with the illumination device 100. As described in more detail below, the embodiments illustrated in FIGS. 1-4, the illumination device 100 includes a knob 132 operable to control volume output of the speaker 130, a knob 134 operable to select a track from the track library 50, a slider 124 operable to select a light color output, and a touch sensor 138 configured to power on/off and control luminance. Those having skill in the art will appreciate upon reading the present disclosure that the type of interface structure and operations controlled by the interface structures may be interchanged and/or implemented using other user interface structures, such as those identified herein or otherwise known in the art.

It is also to be appreciated that the controller 10 may comprise multiple controllers/control devices, such as switches, that may or may not be in communication with one or more other controllers/control devices of the controller 10. Thus, knob 132 may comprise a portion of the controller 10 and may or may not be in communication with other portions of the controller 10 operable to control volume of speaker 130 or operations of other features. For instance, in one example, a user may adjust knob 132 to particular volume setting and initiation of a track from track library 50 may cause the controller 10 to override the volume setting, while in another example the controller 10 may abide by the volume setting upon initiation of a track from the track library 50. Adjustment of knob 132 during output of the track may reduce the volume of sound output.

In various embodiments, the illumination device 100 may comprise an ambient light sensor 122 adapted to sense the presence of light surrounding the illumination device 100, as well as the intensity of such light. The ambient light sensor 122 may be in electrical communication with the light source 120. The luminosity of the light output by light source 120 may be altered dependent on the presence of light received by the ambient light sensor 122. In one example, the ambient light sensor 122 may sense little to no light in the area surrounding the illumination device 100 and signal to the light source 120 to lower the maximum luminosity of the light. Conversely, the ambient light sensor 122 may sense a high presence of light in the area surrounding the illumination device 100 and signal to the light source to increase the maximum luminosity of the light. In one embodiment, the ambient light sensor 122 is wired to the controller 10 of the illumination device 100, which in turn instructs the change of the luminosity of the light output by the light source 120 based upon a determination of the necessary level of light to be output by the light source.

It is to be understood that the illumination device shown in FIG. 7 may include additional or fewer features. With continued reference to FIG. 7 and further reference to FIGS. 1-4, which provide various views of an illumination device 100, wherein like features are identified by like numbers, an illumination device 100 may comprise a housing 110, a light source 120, and a speaker 130. The housing 110 may provide a support structure for the illumination device 100 and house various electrical components of the illumination device 100. The housing 110 may include a front face 112, a back face 114, and a base 116. The base 116 may be positioned below and between the front face 112 and the back face 114. The base 116 may have a relatively flat surface, thereby allowing the housing 110 to stand upright when the base 116 is placed on another surface. However, in other embodiments, the base 116 may comprise other surface dimensions or arrangements such as round, ridged, and/or include one or more projections providing legs, for example. The material of the housing 110 is preferably light-weight and durable, such that it may be easily carried by children and withstand small impacts, such as being dropped on a hard surface. Example housing materials may include plastics, rubbers, hardwoods, lightweight metal, ceramics, or composites.

In the illustrated embodiment, the light source 120 comprises a light emitting diode ("LED"). The LED light source 120 may comprise multiple LEDs. The LEDs are configured to emit light at different frequencies, thereby allowing for the output of different colors of light. The LEDs may also be controllable to output light at deferent intensities. In one example, the LEDs comprises an LED array capable of displaying different colors or color patterns and/or intensities or intensity patterns in response to a control system signal. As introduced above, various light sources 120 may be used. For example, the light source 120 may include one or more light sources such incandescent lights, florescent lights, halogen lights, LED, another light source known in the art, or a combination thereof.

In the illustrated embodiment, the light source 120 is disposed within the housing 110, whereby light output by the light source 120 may emit to the area surrounding the illumination device 100 through a transparent or semi-transparent face along the outer surface 115 of the housing 110. Additionally or alternatively, the light source 120 may be disposed on or along an outer surface 115 of the housing 110.

The housing 110 may further comprise a light diffuser 118, positioned proximate or surrounding the light source 120. The light diffuser 118 may be made of a transparent or translucent material such as, but not limited to, ground glass, frosted glass, acrylics, polycarbonates, light diffusing paper, or other suitable transparent or translucent material known in the art. The light diffuser 118 may comprise a panel or cover forming a portion of the outer surface 115 of the housing 110. In the illustrated embodiment, the light diffuser is configured to evenly scatter and soften light emitted by the light source 120. The light diffuser 118 may be disposed on the housing 110 opposite the base 116, such that the light diffuser 118 is on an upper portion of the housing 110.

In various embodiments, the illumination device 100, or light diffuser 118 thereof, may comprise a touch sensor 138 to provide touch-sensitive capabilities upon the touch of a user that causes the controller 10 to control operations of the illumination device 100. As introduced above, the controller 10 may comprise multiple controllers/control devices, such as switches, that may or may not be in communication with one or more other controllers/control devices. For example, a touch sensor 138 of user interface 30 may be in electrical communication with the light source 120 and/or the speaker 130 via the controller 10, which may include one or more control devices as described herein. Presence of touch may be detected by the touch sensor 138 through pressure applied to the surface of the light diffuser 118, vibration, or capacitance, thereby activating an internal switch within the light diffuser 118. For example, the touch sensor 138 may detect presence of touch, such a finger, when the finger acts as an electrical conductor to complete an electric circuit in electrical communication with the light diffuser 118, which is processed by the controller 10 to identify a control instruction provided by the user. In one embodiment, the touch sensor 138 is operable to switch the light source 120 and/or the speaker 130 on and off through a predetermined touch pattern. For example, a double-tap of the light diffuser 118 may instruct the light source 120 and the speaker 130 to turn on at the last known volume and luminosity and a further double-tap of the light diffuser 118 may instruct the light source 120 and the speaker 130 to turn off. In a further or another example, the touch sensor 138 may be operable to interface the user with luminosity settings. For example, touch or presence detected by the touch sensor 138 may be used to cycle through varying luminosities of the light source 120. In one example, the touch sensor 138 housed in the light diffuser 118 may detect a presence of touch for a predetermined length of time and instruct the light source 120 to gradually increase and then decrease its luminosity until a desired level is achieved and the presence of touch is removed. The gradual change in luminosity is preferably marked by perceptually smooth increases and decreases rather than sudden spaced apart interval steps. It is to be appreciated that touch sensors 134 and/or additional touch sensors may be located at other positions along the housing 100, such as outer surface 115 thereof.

The speaker 130 may be disposed along the outer face 115 of the housing 110, allowing for the output of sound to the area surrounding the illumination device 100. The speaker 130 may be configured to produce intelligible speech, music, or noise. In one embodiment, the speaker 130 may be configured to output white noise, e.g., according to a track in the track library. 50 White noise is noise that has the same intensity throughout the audible frequency range (typically 20 to 20,000 hertz). Thus, white noise may be considered as consisting of low-, medium-, and high-frequency sounds played together at the same intensity level. White noise may assist a person in sleeping by masking sudden consistency changes in sound.

As introduced above, the user interface 30 of the illumination device 100 may include various interface structures in addition to or instead of touch sensor 138. In the illustrated embodiment, the user interface 30 includes a knob 132 adapted to change the volume output by the speaker 130. The volume knob 132 may have a fixed start point and a fixed stop point correlated with a minimum and maximum volume of sound output by the speaker 130, respectively. Alternatively, the volume knob 132 may have no start or stop points and volume may be increased to a maximum volume by clockwise rotation of the volume knob 132 and decreased to a minimum volume by counterclockwise rotation of the volume knob 132. Further rotation upon achieving the maximum or minimum volume would have no effect.

The user interface 30 of the illumination device 100 may comprise a knob 134 adapted to select a track from the track library 50 or otherwise change noise output by the speaker 130. While white noise is considered to have an equal intensity throughout the audible frequency range, pink noise has higher intensities at lower frequency ranges and lower intensities at higher frequency ranges. Brown noise outputs even lower intensity than pink noise at higher frequency ranges. Intensity of noise is often described by the noise's power spectral density, which describes the distribution of power into frequency components composing the noise signal. White noise has a constant power spectral density. Pink noise has a power spectral density that is inversely proportional to the frequency of the noise (i.e. 1/f), such that each octave interval carries an equal amount of noise energy. For Brown noise, the power spectral density is inversely proportional to the square of the frequency of the noise (i.e. $1/f^2$).

Turing of the knob 134 may change the intensities of higher frequency sounds output by the speaker 130, thereby allowing a selection of white, pink, or Brown noise. In one embodiment, the knob 134 may have fixed start point and a fixed stop point correlated with white noise and Brown noise, respectively, with pink noise correlated to a point therebetween. Turning of the knob 134 may gradually decrease or increase the intensity of noise at the higher frequency ranges, such that a user may select different noise output in the white, pink, and Brown noise ranges. In another embodiment, the knob 134 may have no start or stop points and an intensity of high-frequency ranges may be increased to correlate with white noise by clockwise rotation of the knob 134 and decreased to correlate with Brown noise by counterclockwise rotation of the knob 134. Further rotation upon achieving the maximum or minimum intensity levels would have no effect.

The knob 132 and/or the knob 134 may comprise internal tabs that produce a click-sound when rotated by a predetermined amount of degrees. In one example, knob 132 produces a click-sound when it is rotated 30 degrees, allowing for a total of 12 clicks in a single rotation, which advises a user of how far the knob 132 has been rotated. This may be used to select a desired noise output/track (or level of volume for the knob 132) based upon the number of clicks needed to achieve such output. Although knob 132 and knob 134 are disclosed as knobs, volume and noise output/track selection may be selected via use of buttons, switches, a sliding mechanism, or other interface structures known in the art.

In one embodiment, the speaker 130 may be configured to output various sound patterns comprising white noise and/or other color noise such as Brown or pink. For example, the speaker 130 may output a sound pattern by varying the volume of the noise output in accordance with a predetermined cadence, e.g., as defined by a track in the track library 50. The sound pattern may be a breathing pattern having a defined cadence or noise output configured to imitate a breathing rhythm, comprising an inhalation period and an exhalation period. For example, volume of noise output by the speaker 130 may increase during an inhalation period to a maximum volume and the volume of the noise output by the speaker 130 may thereafter decrease during an exhalation period to a minimum volume.

In a further or another embodiment, a breathing pattern may include maintaining output volume approximately constant, while the intensity of noise in the high-frequency range increases and decreases in a cadence representative of a breathing pattern. For example, the intensity of noise in the high-frequency range may increase during the inhalation period until white noise is achieved. The intensity of noise in the high-frequency range may then decrease during the exhalation period, passing through the pink noise range and ending in Brown noise at the completion of the exhalation period. Alternatively, the change in the intensity of noise at the high-frequency range may simply cycle between white noise and pink noise, between pink noise and Brown noise, or between any other known noise ranges, including blue noise, violet noise, or grey noise. Alternatively, the breathing may be a recording of a person's breath, or a synthetically generated sound of the same.

The inhalation period and exhalation period together may be considered a single cadence cycle. A cadence cycle may be in the range between 3 seconds and 8 seconds, for example, wherein the inhalation period accounts for approximately 40% of the cadence cycle, and the exhalation period accounts for 60%. However, in alternative embodiments, the inhalation period may comprise anywhere between 30% to 50% of the cadence cycle, while the exhalation period may account for 70% to 50% of the cadence cycle. In some embodiments, cadence cycle and/or inhalation and exhalation periods thereof may be varied and be tailored to the individual's needs. The length of the cadence and the ratio between inhalation and exhalation may also vary during a session to help bring rapid breathing down (calming effect). For example, the length and duration of the periods may be customizable by the end user, or dynamically changed based on the user's breathing pattern. Such pattern can be detected using a breathing detection device, such as a sound sensor, motion sensor, optical sensor, or other sensor, in the device, or provided by other devices (e.g. sensor in the bed, smart watch, etc.).

In various embodiments, the illumination device 100 may be configured to allow a user to select a particular cadence cycle or length of cadence cycle. For example, the track library 50 may include a plurality of breathing pattern tracks having different breathing cadence cycles. The illumination device 100 may comprise a button or other interface structure that a user may interface to select a desired breathing pattern having a predefined length of cadence cycle. For example, in the illustrated embodiment, knob 134 is operable to select one of a plurality of breathing pattern tracks, each corresponding to a different cadence cycle. In one example, the illumination device 100 may allow for the selection of an approximately 3.5-second cycle, approximately 5-second cycle, or approximately 7-second cycle. The inhalation period in each cycle may be between approximately 35% and approximately 45% of the cycle. For example, cadence cycles may include approximately 1 seconds inhalation and approximately 2.5 seconds exhalation, approximately 1.5 seconds inhalation and approximately 3.5 seconds exhalation, and approximately 2 seconds inhalation and approximately 5 seconds exhalation. It is to be appreciated that the illumination device may include other interface structures configured for selecting and/or defining breathing pattern cadences to be output, which may include selection of tracks from the track library 50 having particular cadences or may include more customized defining of cadences along a continuum of cadences. In one example, the illumination device 100 may comprise a slider mechanism, wherein the length of the cadence cycle may be selected between a minimum cadence length and a maximum cadence length. In an above or another example, the illumination device 100 may comprise button or a slider allowing for a selection of a ratio between the length of the inhalation period and the length of the exhalation period. In an above embodiment, or another embodiment, and as described in more detail below, the illumination device 100 may be configured for wired or wireless communication with a remote device 65, such as a smart device, smartphone, smartwatch, personal computer, tablet, or dedicated device. The remote device 65 may be configured with an application 67 operable to provide a user interface to interface a user with the operations of the illumination device 100, which may be an extension of user interface 30. In some embodiments, the application 67 provides the operations configurable via user interface 30 described above as well as additional features. For example, the application 67 may be configured to allow a user to control one or more of sound output, light output, breathing cadence cycle length, breathing cadence cycle patterns, breathing track, breathing type, audio track, breathing period ratio, duration of sound and/or light output, or power on/off. In one embodiment, the application 67 is operable to set a schedule for altering the sound or light at specific times or days. In one embodiment, the application 67 may be used to schedule and/or define timing of sound and/or light outputs with respect to calming a subject with an output breathing cadence. For example, a user may use the application 67 to set a threshold breathing cadence as to when a breathing cadence to be mimicked is to be output. In another or a further example, the application 67 may be used to select or define modification intervals for one or more output cadences and/or threshold breathing cycles that, if detected, cause the controller 10 to initiate output of breathing cadences to soothe or relax the subject. In some embodiments, the choice of breathing cadences may be selected by a user using the application 67 and/or by the controller 10, which, in one example, may utilize artificial intelligence as described herein. In another or a further example, the application 67 may be used to define a target breathing cycle of the individual that corresponds to when the subject is asleep. In a further example, the controller 10 may discontinue output of sound and/or light when the target breathing cycle has been achieved, which, in one embodiment, may be based on detection of the subject's breathing cycle using breathing detection device 136, which, for example, may be a sound sensor (e.g., microphone), motion sensor (e.g., vibration sensor), optical sensor (e.g., video), or other sensor (e.g., radar, lidar). In one example, the controller 10 utilizes artificial intelligence based on analysis of the individual, detected breathing cycle, mood, or state of exhilaration to determine what the target breathing cycle and/or breathing cycle progression should be. In some embodiments, the application 67 may be operable to upload audio tracks such as recordings of a caregiver's voice or breathing. In one configuration, the application allows a user to view battery life.

The luminosity of the light output by the light source 120 may increase during the inhalation period and decrease during the exhalation period, wherein the luminosity of the light reaches a maximum luminosity at the end of the inhalation period and reaches a minimum luminosity at the end of the exhalation period. In one embodiment, the maximum luminosity is the maximum luminosity capable of being output by the light source 120, and the minimum luminosity is between 30% and 60% of the maximum luminosity. Alternatively, the maximum luminosity may be preset below maximum luminosity capable of being output by the light source 120 or may be selected by the user via interface structures of the user interface 30, such as buttons, knobs, switches, a slider mechanism, or the like. In another embodiment, the minimum luminosity may be configured such that the light source 120 outputs no light at the minimum luminosity.

In one embodiment, the user interface 30 includes an interface structure operable to allow a user to modify the color of the light output by the light source 120. In the illustrated embodiment, the user interface 30 of the illumination device 100 includes a slider 124 adapted to alter the color of the light emitted from the light source 120. The slider 124 may have a path along which it may slide between a start point and end point. As the slider 124 moves from the start point to the end point, different color light elements of the light source 120 (such as white, blue, red, and green LEDs) may be activated and intensities may be modified dependent on the location of the color slider 124 between the start point and end point to achieve different output colors. In one example, when the slider 124 is placed at the start point, the light emitted from the light source 120 is violet in appearance. As the slider 124 is moved towards the end point, the color of the emitted light changes in relation to the visible light spectrum, such that the color transitions from violet to indigo, to blue, to green, to yellow, to orange, and then to red at the end point. In another example, the start point may be configured to emit white light from the light source 120, and transitioning the color slider 124 towards the end point may arbitrarily vary the color of the light based upon predetermined instructions that activate the various light elements of the light source 120. Although disclosed as a slider, other interface structures could be employed such as a knob, buttons, switches, or other configurations known in the art that may allow a user to cycle through different colors available to the light source 120.

In one embodiment, the illumination device 100 may receive electrical power from a wired connection, such as a USB cord or a wired plug extending from the back face 114 of the housing 110 that is adapted to be received by an electrical outlet. In another embodiment, the housing 110 may include a battery 119 for storing electrical energy for powering the electrical components of the illumination device 100. The battery 119 may be one or more disposable batteries, such as standard AA or AAA batteries, or the battery may be a rechargeable battery. Example rechargeable batteries include a lithium-ion battery or a lithium-ion polymer battery. The rechargeable battery 119 may be recharged through a wired connection between a battery port disposed on the back, or bottom, face 114 of the housing or the battery 119 may be wirelessly charged via electromagnetic induction.

Figure 1:
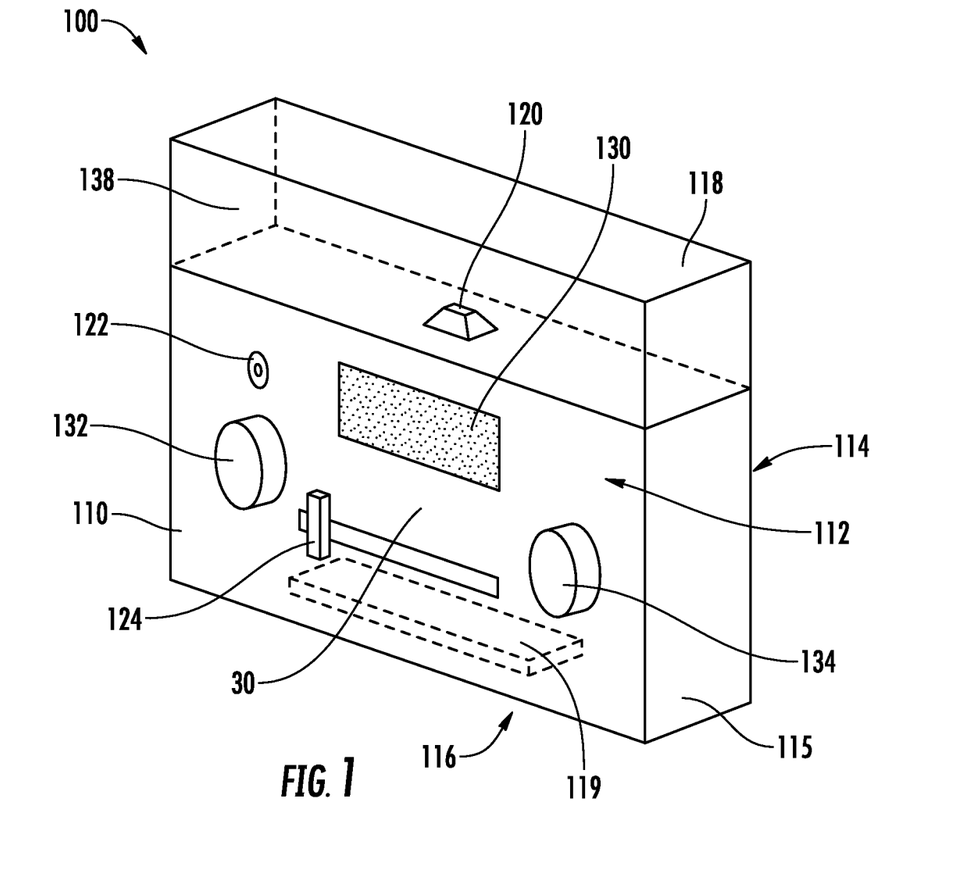
FIG. 1 is a front perspective view of the illumination device in accordance with one embodiment of this disclosure.
Figure 2:
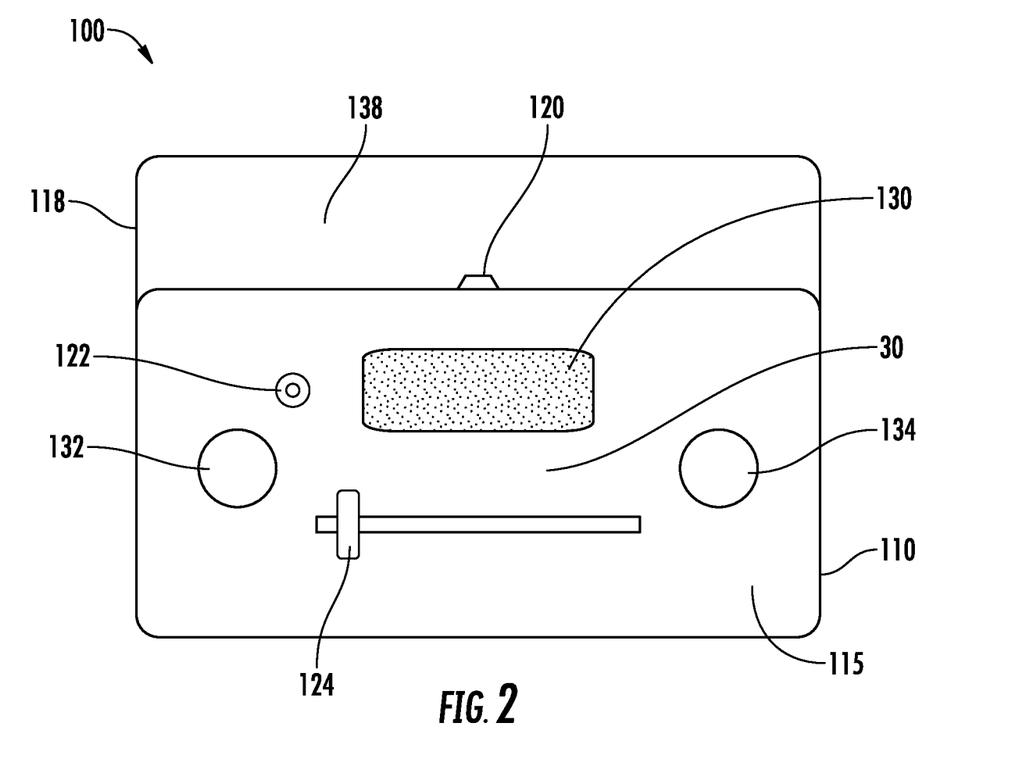
FIG. 2 is a front view of the illumination device in accordance with one embodiment of the disclosure.
Figure 3:
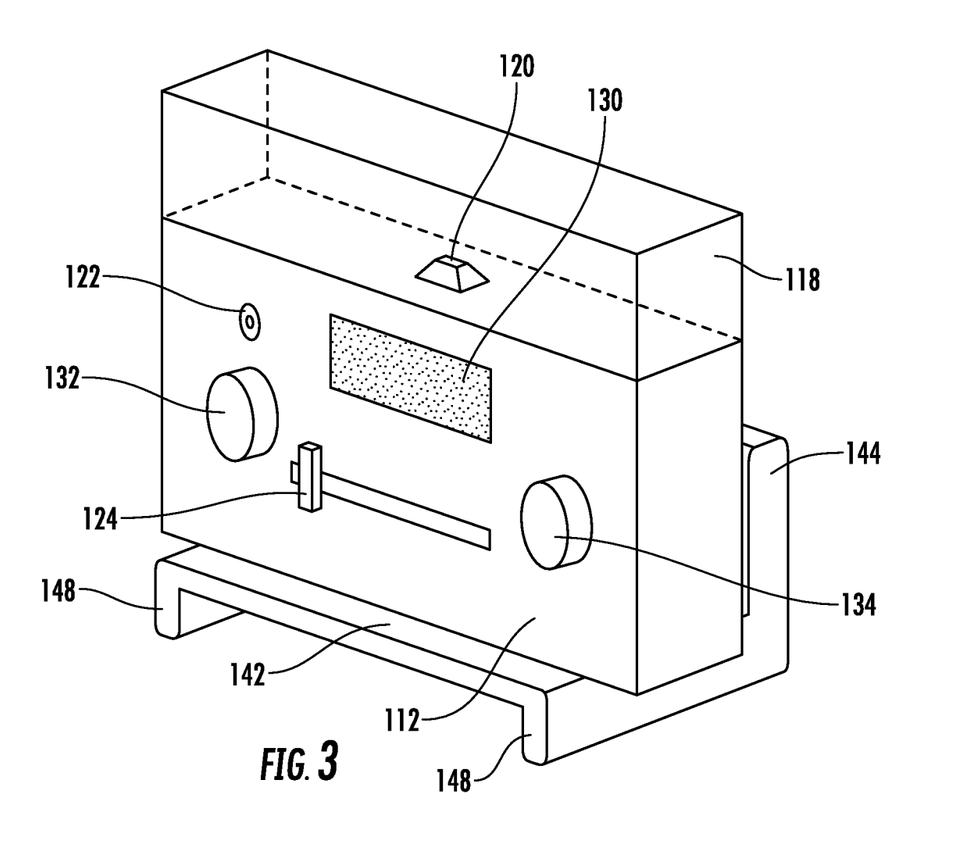
FIG. 3 is a perspective view of the illumination device situated in a stand in accordance with one embodiment of the disclosure.
Figure 4:
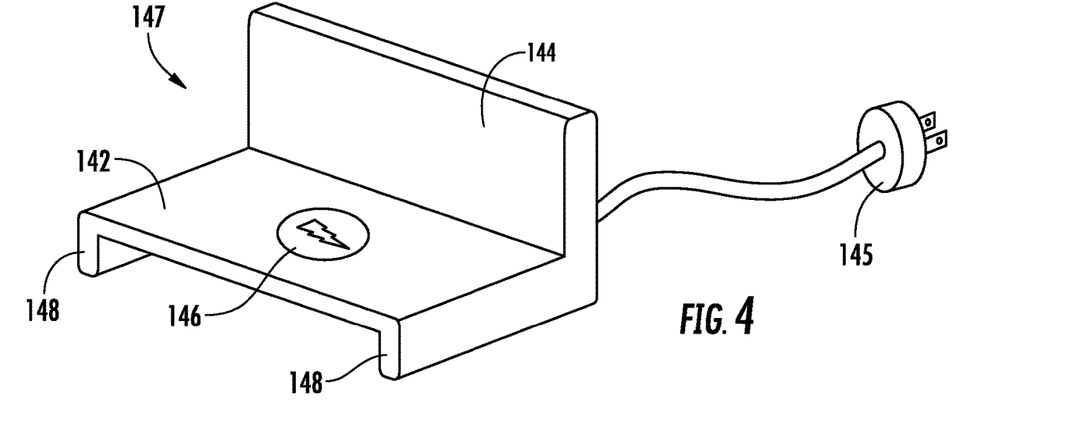
FIG. 4 is a perspective view of the stand in accordance with one embodiment of the disclosure.

In some embodiments, the illumination device 100 may comprise a stand 140 adapted to receive and support the housing 110. With reference to FIGS. 3 & 4, the stand 140 may comprise a support 142 and a back wall 144. The base 116 of the housing 110 may rest upon the support 142 of the stand 140, while the back face 116 of the housing 110 may lean against the back wall 144 of the stand 140. The stand 140 may further comprise legs 148. Legs 148 may be fitted with anti-slip padding on a bottom face, allowing for increased stability. In one embodiment, the stand 140 further comprises protrusions on the support 142 corresponding with recesses in the base 116 of the housing 110, which may allow the housing 110 to sufficiently align with the stand 140.

In various embodiments, the illumination device includes a power supply connector 145 configured to provide power to charge battery 119. The power supply connector 145 may include a plug that plugs between an residential outlet and a battery port in the housing 110. In one embodiment, the stand 140 is equipped with the power supply connector 145 and may comprise a charging dock 146. For example, the power supply connector 145 may be incorporated within the support 142. The charging dock 146 is preferably configured to wirelessly charge the battery 119 when the housing 110 is placed upon the support 142 of the stand 140. For example, the stand 140 may comprise an internal transmitting coil proximate the support 142, and the housing 110 may comprise a receiving coil proximate the base 116. An alternating current running through the transmitting coil of the stand 140 creates an oscillating magnetic field, which, in turn, creates an alternating current in the receiving coil of the housing 110. The alternating current in the receiving coil may then be converted to direct current and diverted to the battery 119 in order to charge the battery 119. The battery 119 may store energy provided by the direct current and use such energy to power the electrical components of the housing 110 when the housing 110 is removed from the stand 140. In one embodiment, the stand 140 further comprises a switch 143, whereby the stand 140 can detect the presence of the housing 110 situated upon the support 142 of the stand 140. The switch 143 may include and optical or light operated switch 143 that closes when the housing 110 positions over a switch sensor and opens when the housing 110 is removed. The switch 143 may include a magnetic switch. When the housing 110 is placed on the stand 140, the magnetic switch 143 is closed, allowing for current to be supplied to electrical components through contacts-, enabling power transfer between the stand 140 and the body 110. When the body 110 is removed from the stand 140 or not properly aligned on the stand 140, the magnetic switch 143 is opened, thereby disallowing the transmission of power from the stand 140. Other switch 143 configurations may be used, such as a switch 143 that operates as above via detection of presence of the housing 110, e.g., utilizing capacitance, or through another methodology known in the art. Such a configuration may provide an additional safety feature for users of the illumination device 100. In various embodiments, the illumination device 100 may not include a stand 140, a charging port 110, or a stand 140 including a charging dock 146.

In one embodiment, the illumination device includes a communication port 65 comprising a receiver or transceiver. The communication port 65 may be configured to provide wired or wireless communication with the controller 10 or the illumination device 100. For example, the communication port 60 may be configured for wired or wireless communication with a remote device. The remote device may comprise a mobile device, smartphone, smartwatch, smart home device, personal computer, tablet, or dedicated device, for example. The remote device may have an operating system that may be iOS, Android, and the like. The application may enable interactions with the illumination device 100.

The communication port 60 may be configured for wireless communication with the remote device 65 to interface operations via suitable wireless communication protocols such as Bluetooth, WiFi or Near-Field Communication (NFC). For example, in one embodiment, the communication port 65 is configured for wireless communication with a remote device 65 via Near-Field Communication (NFC). As the illumination device may be used in close proximity to a child, use of NFC may be used to avoid radiation concerns. Thus, in such an example, a remote device may interface a user with the operations of the illumination device 100 via NFC. In a further or another embodiment, the communication port 60 may be configured for wired communication. For example, the remote device 65 may wire directly to the communication port along the housing 110, such as through the use of a universal serial bus (USB).

The remote device 65 may be configured with or be operable to utilize an application 67, such as a mobile application, configured to interface the user with the illumination device 100 via the remote device 65. The application 67 may include instructions that when executed by a processor cause the operations of the application 67. The application may include software or firmware, for example.

As noted above, the application 67 may provide a user interface, which may allow the user to configure various outputs of the illumination device 10, such as altering the volume, increasing or decreasing the maximum intensity of the light, changing the color of the light, or altering the sound output by the speaker 130. In one embodiment, the application 67 may be used to upload user-selected or recorded sounds to the track library 50, such as prerecorded music, audiobooks, or soothing sounds.

As noted above, the application 67 may interface users with operations of the illumination device 100. Such operations may include those interactions that may be enabled directly from the illumination device 100, e.g., via user interface 30, or may be additional.

The application 67 may be operable to provide setting or instructions for controlling operations such as one or more of changing of the volume of the sound output by the speaker 130, selection of a track, changing the cadence of the sound output by the speaker 130, adjusting the maximum luminosity of the light emitted by the light source 120, altering the color of light emitted by the light source 120 or the like. Further to the above or in another example, the application 67 may allow a user to choose alternative tracks, such as sounds that can output by the speaker 130, e.g., recorded music, lullabies, audiobooks, sounds of falling rain, or the like, to be downloaded to the track library 50 of the illumination device 100. In any of the above or another example, the application 67 may be used to change user interface 30 operations such as the output operations controlled by the various control devices, such as buttons, switches, knobs, or sliders. In various embodiments, the communication between the remote device 65 and communication port 60 is two-way. For example, a user may use the remote device 65 to query the illumination device with the application 67 for battery life, operation history, or to view or modify tracks in the track library 50.

In some embodiments, the application 67 is configured to override operations provided by the user interface 30 located along the housing 110 to prevent a child from overriding remote instructions. In one example, the override is temporary for a predetermined time period after a setting or instruction is provided by the application 67, such a day or week, in case the remote device 65 or application 67 is lost or unusable. Thus, following a period of time the operation of the illumination device 100 with respect to the setting or instruction may be returned to a standard or pre-instruction setting. In some embodiments, operation at the user interface 30 along the housing 110 may override all or some of the settings or instructions provided by the application or just those settings or instructions specified by a user via the application 67. In one example, the application 67 allows configuring of maximum volume, maximum luminosity, sound or light durations, on/off times, or the like. In one example, the communication port is configured to provide NFC or other wireless communication with a remote user interface 30 provided by a remove device 65 running application 67. The user may one or more of turn the illumination device 100 (e.g., one or more of light output or speaker output), transfer a schedule modifying or defining times the illumination device is to turn on or off (which, in one example, may include defining times for light output power separate from sound output power), define luminosity settings of light output from the light source, define sound output settings from the speaker, define color settings of light output from the light source, transfer a sound track to the track library for output from the speaker, or update time and/or date.

The present disclosure may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure. For example, the housing 110 further may include a breathing detection device 136 to detect breathing. The illustrated embodiment will be described with respect to a breathing detection device comprising a microphone, however, other breathing detection devices 136 may be used such as motion sensors (e.g., vibration sensor), optical sensors (e.g., video), or other sensors (e.g., radar, lidar). The microphone is capable of receiving sound from the area surrounding the illumination device 100. The microphone may detect breathing sound of a subject, and the controller 12 may analyze the sounds to determine if the sounds correspond to breathing. A sound signal, representative of the sound from the area surrounding the illumination device 100, may then be provided to the controller 10, which may process and analyze characteristics of the sound signal to determine whether a breathing pattern is present in the sound. The controller 12 may also analyze characteristics of the breathing to determine if the subject is relaxed, upset, excited, or the like. Characteristics may include length of breathing cycles, ratio of inhalation and exhalation periods within cycles, breathing depth, consistency of the same, or the like. For example, short breathing cycles and periods within the cycles may indicated the subject is in an excited or upset state, or a non-relaxed or soothed state. The controller 12 may then output a breathing cadence for the subject to mimic that is targeted to increase the length of the subject's breathing cycles, to thereby relax or soothe the subject. The controller may similarly output a breathing cadence targeted at modifying the subject's inhalation and exhalation periods. The controller 12 may be configured to select a cadence that progressively increases cycle length over time. Alternatively, the controller 12 may be configured to dynamically modify cycle length and/or ratio of inhalation period to exhalation period within cycles of the cadence during output of the breathing noise for the subject to mimic based on characteristics of breathing sounds. For example, in some embodiments, the controller 12 may progressively increase cycle duration by a set duration over the detected breathing cycle duration to relax or soothe the subject. In one embodiment, if a breathing pattern is determined to be present in the sound, the controller 10 may determine the cadence of the detected breathing pattern should be modified. For example, if length of a breathing cycle is short or ratio of inhalation to exhalation periods is determined to be short, the controller 10 may cause output a slightly longer cadence for the subject to mimic. Thereafter, the cadence may become progressively longer to soothe and relax the subject. As introduced above, such progression may be programmically set or may be dynamic based on continued analysis of the subject's breathing. In various embodiments, a user may configured, e.g., via operation at the user interface 30 along the housing 110 or an application, breathing characteristics in which the controller 10 is to respond, set increase in cycle duration above those detected of a subject, duration of breathing noise output, target cycle length and/or period ratio in which to discontinue increase or modification of output, or target cycle length and/or period ratio in which to discontinue one or more of noise output or light output. In another example, if a breathing pattern is determined to be present in the sound, the controller 10 may determine if the cadence of the detected breathing pattern is below a threshold and may output a slightly longer cadence for the subject to mimic. In any of the above examples or another example, the controller 10 may modify the ratio of inhalation to exhalation periods, e.g., to progressively increase inhalation period output relative to exhalation period output. In a further example, the cadence may become progressively longer to soothe and relax the subject. In some embodiments, the controller 12 is configured to discontinue output of the breathing noise when detected breathing indicates that the subject is soothed and/or asleep.

Further to the above, in some embodiments, the controller 10 may adjust output cadence to match that of the subject. The controller 10 may then progressively modify the cadence to attempt to cause the subject to similarly modify their breathing cycle to match that of the output. For example, the controller 10 may use the microphone, a motion detection device, or other suitable device to detect a subject's breathing. If the detected length of the breathing cycle is below a threshold, the controller 10 may cause output of a breathing cadence that corresponds to the subjects and then progressively lengthen the output cadence to relax or soothe the subject. The progression may be a pre-determined progression such that a set calming track having a predefined increase in breathing cycle length is output. The selection of a calming track or starting point of the calming track to be output may be based on initially matching the cadence of the detected breathing cycle. In another example, the calming track selection or starting point within a calming track that is output may be at a slightly longer breathing cycle than that detected.

In one embodiment, the controller 10 may dynamically change the cadence of a breathing cycle output. For example, the controller 10 may analyze a subject's breathing pattern to determine if the subject is mimicking the output cadence. If the subject is, the controller 10 may decrease the cadence a suitable interval. If the subject is not mimicking the output breathing cycle, the controller 10 may increase the output cadence to match that of the subject or increase the output cadence to one slightly longer than that of the subject to attempt to bring the subject in sync with the output cadence. Thereafter, the controller 10 may continue to similarly analyze the subject's breathing patterns and modify the cadence until the subject has achieved a target breathing pattern. Intervals of decrease in breathing cadence or rates of decrease may be predefined, preset, or dynamic. For example, in one embodiment, a number of calming breathing tracks may be provided with different intervals and/or rates of interval changes. In one embodiment, using a user interface 30 along the housing or an application 67 a user may select a track or program of tracks having a cadence progression that utilizes intervals that best suit the subject. In one embodiment, the controller 10 may track how well a subject mimics a cadence and what intervals and/or rates of progression change the subject follows best. The controller 10 may use this data to determine which preset tracks to output or to dynamically change cadence during the output of the breathing cycle. For example, a subject may be determined to be quickly adaptable to a 0.2 second interval decrease when a cadence is 3 seconds and 0.15 second interval decrease at a cadence of 5 seconds. The controller 10 may therefore output breathing cycle cadences that suit the subject to more closely tailor the operations to the subject. In some embodiments, the controller 10 may adjust cadence based on a current detected breathing rate to help the subject relax or fall asleep. In one example, the controller 10 utilizes artificial intelligence to determine what the breathing pattern should look like for the individual subject. In a further example, the artificial intelligence determines what the pattern for the individual should be based on a detected mood or state of exhilaration of the subject. For instance, sound data or motion data corresponding to breathing or crying may be used by the controller 10 in a manner that applies artificial intelligence to determine which cadence progression and/or intervals to use to aid in the subject falling asleep. In a further or another example, the controller 10 utilizes artificial intelligence to determine a target breathing cycle that corresponds to the subject being relaxed or asleep based on the individual, determined mood, or determined state of exhilaration. In one example, when the target breathing cycle is reached, the controller 10 may discontinue sound and/or light output.

While portions of the present disclosure described analysis of subject breathing using sound detection by a microphone associated with a housing 110, in some embodiments, the detection functions described with respect to the microphone may be performed by another breathing detection devices 136 and the controller 10 may similarly analyze and act upon the determined breathing cycle. For example, a motion sensor, such as a vibration sensor or video sensor may be used to detect breathing of a subject for use by the controller 10. In one example, radar or lidar may be used to detect breathing of the subject for use by the controller 10. Such breathing detection devices 136 may be associated with the housing 110 or may be provided separately and be in communication with the controller 10.

Figure 5:
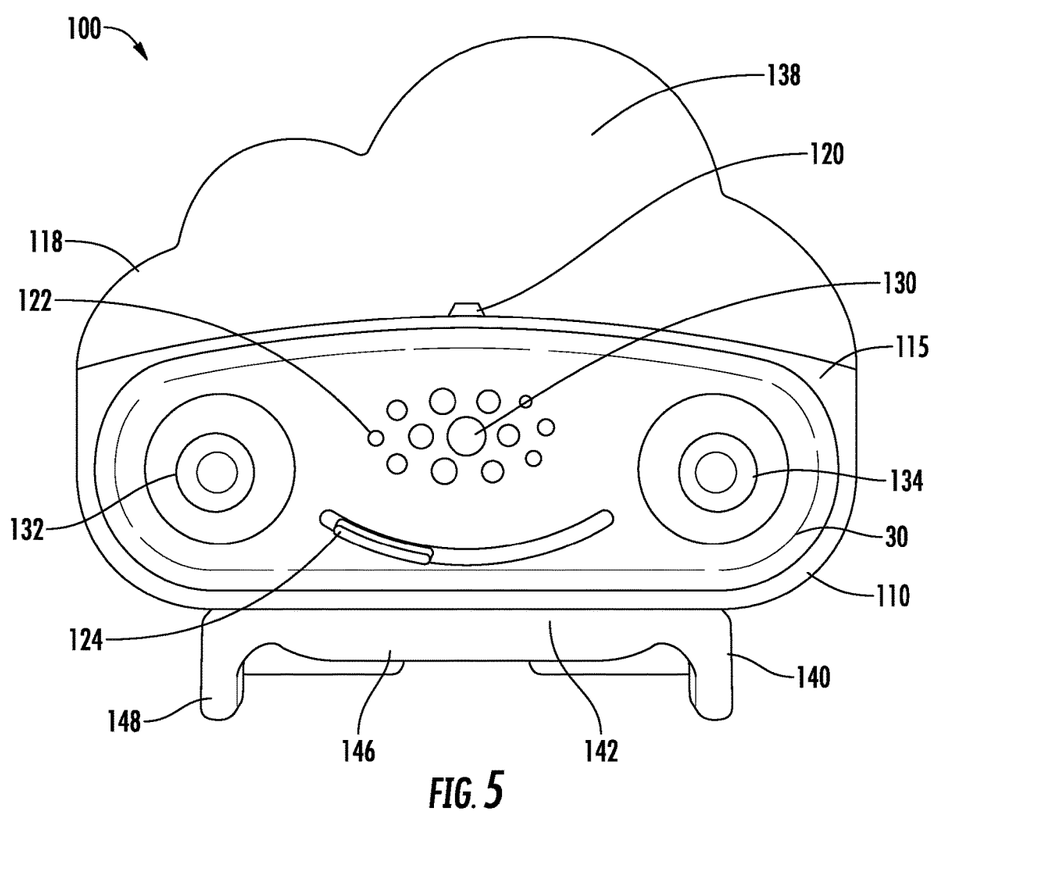
FIG. 5 is a front view of the illumination device in accordance with a second embodiment of the disclosure.
Figure 6:
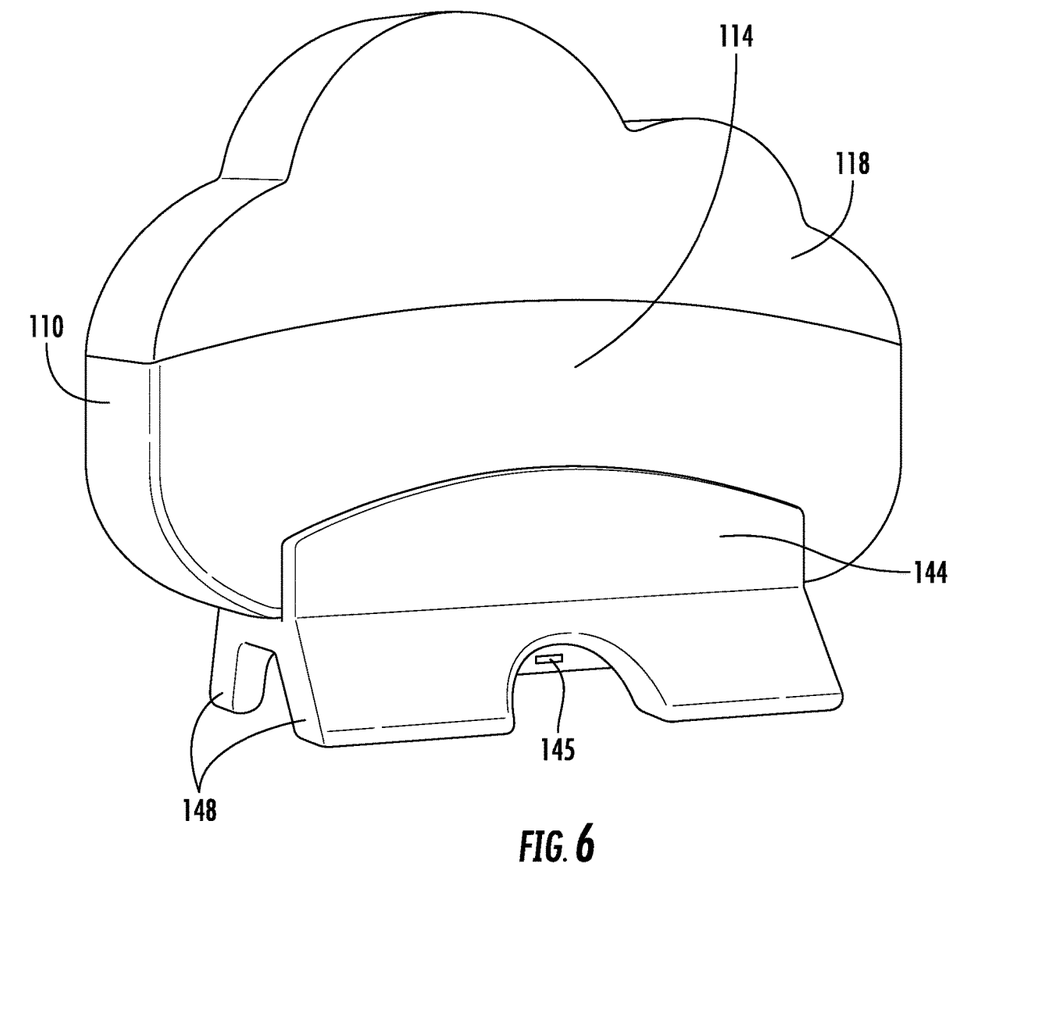
FIG. 6 is a back perspective view of the illumination device of the embodiment disclosed in FIG. 5.

FIGS. 5 & 6 illustrate an exemplary embodiment of the illumination device 100. This illumination device comprises features similar to those described above, in connection with the other disclosed embodiments and figures, wherein like features are identified by like numbers. For example, the illumination device 100 may include the housing 110, light source 120, light diffuser 118, touch sensor 138, speaker 130, knobs 132 and 134, slider 124, stand 140, power supply connector 145, and charging dock 146. In this embodiment, the housing 110 and user interface 30 are configured such that the knobs 132, 134 and slider 124 have the appearance of eyes and a smiling mouth, respectively, so as to create an impression of a smiling figure that is pleasant and attractive to children. Further, the speaker 130 may be arranged as freckles of the figure, wherein one freckle comprises the ambient light sensor 122. The power supply connector 145 may be configured as a USB-C port, wherein one end of a charging cord may plug into the power supply connector 145 and a second end of the charging cord may plug into a residential outlet to supply electrical charge to the charging dock 146 of the stand 140. In this embodiment the charging dock 146 may be situated below the support 142 of the stand 140. Similarly, as shown in FIGS. 5 & 6, the light diffuser 118 may have the appearance of a cloud such that the lighting is attractive to children. The touch sensor 138 may be located on light diffuser 118 and adapted to sense touch on the cloud-like appearance of the light diffuser 118.

This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular preferred arrangements disclosed for carrying out this invention, but that the invention will include all embodiments and arrangements falling within the scope of the appended claims.

Various elements described herein have been described as alternatives or alternative combinations. It is to be appreciated that embodiments may include one, more, or all of any such elements. Thus, this description includes embodiments of all such elements independently and embodiments including such elements in all combinations.

The grammatical articles "one", "a", "an", and "the", as used in this specification, are intended to include "at least one" or "one or more", unless otherwise indicated. Thus, the articles are used in this specification to refer to one or more than one (i.e., to "at least one") of the grammatical objects of the article. By way of example, "a component" means one or more components, and thus, possibly, more than one component is contemplated and may be employed or used in an application of the described embodiments. Further, the use of a singular noun includes the plural, and the use of a plural noun includes the singular, unless the context of the usage requires otherwise. Additionally, the grammatical conjunctions "and" and "or" are used herein according to accepted usage. By way of example, "x and y" refers to "x" and "y". On the other hand, "x or y" refers to "x", "y", or both "x" and "y", whereas "either x or y" refers to exclusivity.

Any numerical range recited herein includes all values and ranges from the lower value to the upper value. For example, if a range is stated as 1 to 50, it is intended that values such as 2 to 40, 10 to 30, 1 to 3, or 2, 25, 39 and the like, are expressly enumerated in this specification. These are only examples of what is specifically intended, and all possible combinations of numerical values and ranges between and including the lowest value and the highest value enumerated are to be considered to be expressly stated in this application. Numbers modified by the term "approximately" or "about" are intended to include +/−10% of the number modified.

What is claimed is:

1. An illumination device comprising:
   a housing;
   a light source associated with the housing;
   a speaker associated with the housing; and
   a controller operable to control sound output of the speaker and light output of the light source,
   wherein the controller is configured to cause the speaker to output a breathing sound pattern in a desired cadence,
   wherein the breathing sound pattern output from the speaker is selected from white noise, brown noise, pink noise, or a recording of a person's breath,
   wherein the controller is configured to cause a luminosity of light emitted from the light source to increase and decrease in synchronization with a volume of the breathing sound pattern output by the speaker,
   wherein the cadence comprises a first period corresponding to an inhalation portion of the breathing sound pattern and a second period corresponding to an exhalation portion of the breathing sound pattern,
   wherein the volume of the breathing sound pattern output by the speaker increases during the first period and decreases during the second period,
   wherein a length of the first period is between 30% and 50% of a single cycle of the cadence and a length of the second period is between 70% and 50% of the single cycle of the cadence.

2. The illumination device of claim 1, wherein a length of the first period is about 40% of a single cycle of the cadence and a length of the second period is about 60% of the single cycle of the cadence.

3. The illumination device of claim 1, further comprising a communication port configured to provide near field communication with a remote user interface operable to one or more of turn the illumination device on and off, transfer a schedule defining times the illumination device is to turn on or off, define luminosity settings of light output from the light source, define sound output settings from the speaker, define color settings of light output from the light source, transfer a sound track for output from the speaker, or update time or date.

4. The illumination device of claim 1, wherein a color of the light output by the light source is adjustable.

5. The illumination device of claim 1, wherein a length of a single cycle of the cadence is between 3 seconds and 7 seconds.

6. The illumination device of claim 1, wherein a length of a single cycle of the cadence is adjustable.

7. The illumination device of claim 1, further comprising a light diffuser proximate the light source, wherein the light diffuser is adapted to soften the light emitted from the light source.

8. The illumination device of claim 1, wherein the illumination device at least one of further comprises a user interface provided along the housing, or is configured to be controlled remotely via an application executed on a remote device.

9. The illumination device of claim 8, wherein the illumination device comprises the user interface, and wherein the user interface is operable to enable a user to change at least one of a cycle length or a ratio of first period to second period within cycles.

10. The illumination device of claim 8, wherein the illumination device comprises the user interface, and wherein the user interface is operable to enable a user to select one of a plurality of colors of light output by the light source.

11. The illumination device of claim 10, wherein the user interface comprises a slider on the housing movable along a slider path to change a color of light output by the light source as the slider transitions from a first end of the slider path to a second end of the slider path.

12. An illumination device comprising:
    a housing;
    a light source associated with the housing;
    a speaker associated with the housing;
    a controller operable to control sound output of the speaker and light output of the light source;
    a battery associated with the housing configured to supply electrical power to the illumination device; and
    a stand adapted to receive the housing and configured to provide electrical power to the device and to charge the battery,
    wherein the controller is configured to cause speaker to output a breathing sound pattern at varying volumes in a desired cadence,
    wherein the breathing sound pattern output from the speaker is selected from white noise, brown noise, pink noise, or a recording of a person's breath, and
    wherein the controller is configured to cause a luminosity of light emitted from the light source to increase and decrease in synchronization with the volume of the breathing sound pattern output by the speaker.

13. The illumination device of claim 12, wherein the stand includes a charging dock configured to wirelessly charge the battery.

14. The illumination device of claim 13, wherein the charging dock includes a switch that is configured to detect when the housing is positioned on the charging dock of the stand for charging.

15. The illumination device of claim 13, wherein the stand includes a magnetically activated switch to disconnect power from contacts of the charging dock that supply power to charge the battery when the device is not coupled to the stand.

16. An illumination device comprising:
  a housing;
  a light source associated with the housing;
  a speaker associated with the housing;
  a controller operable to control sound output of the speaker and light output of the light source; and
  a breathing detection device to detect breathing of a subject within a surrounding environment of the illumination device,
  wherein the controller is configured to cause the speaker to output a breathing sound pattern at varying volumes in a desired cadence,
  wherein the breathing sound pattern output from the speaker is selected from white noise, brown noise, pink noise, or a recording of a person's breath,
  wherein controller is configured to cause a luminosity of light emitted from the light source to increase and decrease in synchronization with the volume of the breathing sound pattern output by the speaker, and
  wherein the controller is configured to analyze the detected breathing and discontinue or alter output of the breathing sound pattern when the detected breathing corresponds to a desired breathing pattern.

17. The illumination device of claim 16, wherein the controller determines what the breathing pattern should be based on desired parameters.

18. An illumination device comprising:
  a housing;
  a light source associated with the housing;
  a speaker associated with the housing;
  a controller operable to control sound output of the speaker and light output of the light source; and
  a breathing detection device to detect breathing of a subject within a surrounding environment of the illumination device,
  wherein the controller is configured to cause the speaker to output a breathing sound pattern at varying volumes in a desired cadence,
  wherein the breathing sound pattern output from the speaker is selected from white noise, brown noise, pink noise, or a recording of a person's breath,
  wherein the controller is configured to cause a luminosity of light emitted from the light source to increase and decrease in synchronization with the volume of the breathing sound pattern output by the speaker, and
  wherein the controller is configured to modify a cycle of an output cadence based on current breathing rate detected by the breathing detection device.

19. The illumination device of claim 18, wherein the controller defines a cadence to output based on desired parameters.

20. An illumination device comprising:
  a housing;
  a light source associated with the housing;
  a speaker associated with the housing; and
  a controller operable to control sound output of the speaker and light output of the light source;
  wherein the controller is configured to cause the speaker to output a breathing sound pattern at varying volumes in a desired cadence,
  wherein the breathing sound pattern output from the speaker is selected from white noise, brown noise, pink noise, or a recording of a person's breath,
  wherein the controller is configured to cause a luminosity of light emitted from the light source to increase and decrease in synchronization with the volume of the breathing sound pattern output by the speaker,
  wherein the cadence comprises a first period corresponding to an inhalation portion of the breathing sound pattern and a second period corresponding to an exhalation portion of the breathing sound pattern, and
  wherein at least one of the cycle length or ratio of first period to second period within cycles of the cadence change during output of the breathing sound pattern.

21. An illumination device comprising:
  a housing;
  a light source associated with the housing;
  a speaker associated with the housing; and
  a controller operable to control sound output of the speaker and light output of the light source; and
  a breathing detection device to detect breathing of a subject within a surrounding environment of the illumination device,
  wherein the controller is configured to cause the speaker to output a breathing sound pattern in a desired cadence,
  wherein the breathing sound pattern output from the speaker is selected from white noise, brown noise, pink noise, or a recording of a person's breath,
  wherein the controller is configured to cause a luminosity of light emitted from the light source to increase and decrease in synchronization with a volume of the sound output by the speaker,
  wherein the cadence comprises a first period corresponding to an inhalation portion of the breathing sound pattern and a second period corresponding to an exhalation portion of the breathing sound pattern, and
  wherein the controller is configured to dynamically modify at least one of a cycle length, or a ratio of the first period to the second period within cycles of the cadence during output of the breathing sound paternn based on characteristics of the subject's breathing detected by the breathing detection device.

22. An illumination device comprising:
  a housing;
  a light source associated with the housing;
  a speaker associated with the housing;
  a controller operable to control sound output of the speaker and light output of the light source; and
  a touch sensor,
  wherein the controller is configured to cause the speaker to output a breathing sound pattern at varying volumes in a desired cadence,
  wherein the breathing sound pattern output from the speaker is selected from white noise, brown noise, pink noise, or a recording of a person's breath,
  wherein the controller is configured to cause a luminosity of light emitted from the light source to increase and decrease in synchronization with the volume of the breathing sound pattern output by the speaker, and
  wherein at least one of:
    a double-tap of the touch sensor is operable to toggle the speaker between an on position and an off position;
    a double-tap of the touch sensor is operable to toggles the speaker and light source between an on position and an off position; or a prolonged touch for a predetermined amount of time sensed by the touch sensor gradually changes a luminosity of the light source until the prolonged touch is removed.

* * * * *